(12) United States Patent
Murdoch et al.

(10) Patent No.: US 11,903,628 B1
(45) Date of Patent: Feb. 20, 2024

(54) KYPHOPLASTY SYSTEM AND METHOD

(71) Applicant: Osteon Medical LLC, Grand Island, NE (US)

(72) Inventors: Nathan William Murdoch, Grand Island, NE (US); Cody L. Evans, Grand Island, NE (US)

(73) Assignee: Osteon Medical LLC, Grand Island, NE (US)

( * ) Notice: Subject to any disclaimer, the term of this patent is extended or adjusted under 35 U.S.C. 154(b) by 0 days.

(21) Appl. No.: 18/137,106

(22) Filed: Apr. 20, 2023

(51) Int. Cl.
*A61B 17/88* (2006.01)

(52) U.S. Cl.
CPC .................. *A61B 17/8855* (2013.01)

(58) Field of Classification Search
CPC .................................................. A61B 17/8855
See application file for complete search history.

(56) References Cited

U.S. PATENT DOCUMENTS

| | | | |
|---|---|---|---|
| 3,601,151 A | 8/1971 | Winnard | |
| 3,731,707 A | 5/1973 | Berle et al. | |
| 3,797,522 A | 3/1974 | Carleton | |
| 3,965,930 A | 6/1976 | Nicholls | |
| 4,346,704 A | 8/1982 | Kulle et al. | |
| 4,364,392 A * | 12/1982 | Strother | A61B 17/0057 606/195 |
| 4,405,249 A | 9/1983 | Scales | |
| 5,064,416 A | 11/1991 | Newgard et al. | |
| 5,571,189 A | 11/1996 | Kuslich et al. | |
| 5,935,110 A | 8/1999 | Brimhall | |
| 6,042,380 A | 3/2000 | Rowe | |
| 6,056,718 A | 5/2000 | Funderburk et al. | |
| 6,127,597 A | 10/2000 | Beyar et al. | |
| 6,395,007 B1 | 5/2002 | Bhatnagar et al. | |
| 6,450,973 B1 | 9/2002 | Murphy | |
| 6,561,724 B1 | 5/2003 | Carletti | |
| 6,572,586 B1 | 6/2003 | Wojcik | |
| 6,716,216 B1 * | 4/2004 | Boucher | A61B 17/1631 606/86 R |
| 6,719,726 B2 | 4/2004 | Meng et al. | |
| 7,556,650 B2 | 7/2009 | Collins et al. | |
| 7,628,800 B2 | 12/2009 | Sherman et al. | |
| 7,666,205 B2 | 2/2010 | Weikel et al. | |
| 7,713,250 B2 * | 5/2010 | Harding | A61M 39/26 251/149.3 |

(Continued)

FOREIGN PATENT DOCUMENTS

| | | | |
|---|---|---|---|
| EP | 3470000 | 4/2019 | |
| WO | WO-2007056498 A2 * | 5/2007 | ........... A61N 5/0601 |

(Continued)

OTHER PUBLICATIONS

Cornelis et al., "Innovative spine implants for improved augmentation and stability in neoplastic vertebral compression fracture," Medicina, Aug. 2019, 55(8):426.

(Continued)

*Primary Examiner* — Zade Coley
(74) *Attorney, Agent, or Firm* — Fish & Richardson P.C.

(57) ABSTRACT

A kyphoplasty system disclosed herein includes various instruments which can be selectively used to perform a kyphoplasty operation on a patient. For example, in some embodiments the kyphoplasty system includes an improved detachment mechanism between the balloon implant and its delivery shaft.

20 Claims, 9 Drawing Sheets

(56) References Cited

U.S. PATENT DOCUMENTS

| | | | |
|---|---|---|---|
| 7,798,994 | B2 | 9/2010 | Brimhall |
| 8,038,682 | B2 | 10/2011 | McGill et al. |
| 8,403,937 | B2 | 3/2013 | Schwardt et al. |
| 8,491,591 | B2 * | 7/2013 | Furderer ............ A61B 17/7097 606/86 R |
| 8,647,378 | B2 | 2/2014 | Mews et al. |
| 8,652,104 | B2 | 2/2014 | Goral et al. |
| 8,870,888 | B2 | 10/2014 | Steffen et al. |
| 8,900,304 | B1 * | 12/2014 | Alobaid ............ A61B 17/7097 606/92 |
| 8,986,386 | B2 | 3/2015 | Oglaza et al. |
| 9,283,018 | B1 | 3/2016 | Alobaid |
| 9,358,058 | B2 | 6/2016 | O'Halloran et al. |
| 9,414,933 | B2 | 8/2016 | Banouskou |
| 9,545,495 | B2 | 1/2017 | Goral et al. |
| 9,579,130 | B2 | 2/2017 | Oglaza et al. |
| 10,820,933 | B1 * | 11/2020 | Murdoch ............ G09B 23/285 |
| 10,821,002 | B1 | 11/2020 | Hibri |
| 10,881,522 | B2 | 1/2021 | Hibri |
| 11,051,862 | B2 * | 7/2021 | Fuerderer ............ A61B 17/8858 |
| 11,058,430 | B2 * | 7/2021 | Gorochow ....... A61B 17/12113 |
| 11,103,290 | B1 * | 8/2021 | Murdoch ........... A61B 17/8855 |
| 11,246,633 | B1 * | 2/2022 | Murdoch ............ A61B 17/7097 |
| 11,311,325 | B2 | 4/2022 | Murdoch et al. |
| 11,413,079 | B2 | 8/2022 | Murdoch et al. |
| 11,576,711 | B2 | 2/2023 | Murdoch et al. |
| 11,596,460 | B2 | 3/2023 | Murdoch et al. |
| 2002/0049448 | A1 | 4/2002 | Sand et al. |
| 2005/0245938 | A1 | 11/2005 | Kochan |
| 2006/0079905 | A1 | 4/2006 | Beyar |
| 2006/0100706 | A1 | 5/2006 | Shadduck et al. |
| 2007/0293866 | A1 | 12/2007 | Stoeckel et al. |
| 2008/0140014 | A1 | 6/2008 | Miller et al. |
| 2008/0249509 | A1 | 10/2008 | Glenn |
| 2009/0062744 | A1 | 3/2009 | Weilbacher et al. |
| 2010/0198225 | A1 | 8/2010 | Thompson et al. |
| 2010/0249933 | A1 | 9/2010 | Trieu |
| 2010/0284734 | A1 | 11/2010 | Turnour |
| 2011/0202064 | A1 | 8/2011 | O'Halloran et al. |
| 2012/0010624 | A1 * | 1/2012 | O'Halloran ........ A61B 17/8805 606/94 |
| 2012/0197204 | A1 | 8/2012 | Helm, Jr. |
| 2012/0259375 | A1 | 10/2012 | Druma et al. |
| 2013/0041256 | A1 | 2/2013 | Fiebig et al. |
| 2013/0345765 | A1 | 12/2013 | Brockman et al. |
| 2014/0257239 | A1 | 9/2014 | Arthur et al. |
| 2015/0012002 | A1 | 1/2015 | Steffen et al. |
| 2015/0201963 | A1 | 7/2015 | Snow |
| 2016/0220790 | A1 | 8/2016 | Borowicz |
| 2017/0252077 | A1 | 9/2017 | DiPoto et al. |
| 2018/0092662 | A1 | 4/2018 | Rioux et al. |
| 2018/0256188 | A1 | 9/2018 | Goshayeshgar |
| 2019/0167333 | A1 | 6/2019 | Druma |
| 2019/0247027 | A1 | 8/2019 | Brown et al. |
| 2021/0015531 | A1 | 1/2021 | Murdoch et al. |
| 2021/0015532 | A1 | 1/2021 | Murdoch et al. |
| 2021/0015533 | A1 | 1/2021 | Murdoch et al. |
| 2021/0015534 | A1 | 1/2021 | Murdoch et al. |
| 2021/0045788 | A1 | 2/2021 | Murdoch et al. |
| 2022/0233219 | A1 | 7/2022 | Murdoch et al. |

FOREIGN PATENT DOCUMENTS

| | | |
|---|---|---|
| WO | WO 2019/133775 | 7/2019 |
| WO | WO-2023076529 A1 * | 5/2023 |

OTHER PUBLICATIONS

DePuy Synthes, "VBS—Vertebral Body Stenting System: Surgical Technique," from URL <http://synthes.vo.llnwd.net/o16/LLNWMB8/INT%20Mobile/Synthes%20International/SGT-EMEA-Agile/SE_818940AA/SE_818940AAeng.pdf>, Nov. 2020, 27 pages.

izimed.com, "Kiva VCF Treatment System: The Implant Solution for Restoration of Sagittal Alignment," from URL <https://static1.squarespace.com/static/5cba31329b8fe86db05fc0eb/t/5d922d0d7ee00f102eb54317/1569860889779/L127+KIVA+Surgeon+Brochure%2C+Rev.+B.pdf>, Sep. 9, 2019, 8 pages.

Medtronic. [Online]"Kyphon Balloon Kyphoplasty: A minimally Invasive Treatment for Spinal Fractures," Copyright 2011 [Retrieved on Aug. 7, 2019] Retrieved from Internet: URL<http://www.back.com/wcm/groups/mdtcom_sg/mdt/back/neuro/documents/documents/contrib_186028.pdf> 20 pages.

PCT International Search Report and Written Opinion in International Appln. No. PCT/US2022/013281, dated May 19, 2022, 16 pages.

Strykier. [Online] "iVAS Inflatable Vertebral Augmentation System: Procedure Overview," Copyright 2011, Brochure Available on or before Sep. 2, 2018 [Retrieved on Aug. 7, 2019] Retrieved from Internet: URL<https://pain-doc.co.uk/wp-content/uploads/2017/11/Procedure_Overview.pdf> 6 pages.

Vexim. [Online] "SpineJack: Controlled Anatomical Respiration: Introducing the surgical technique," Available on or before Jul. 15, 2019, [Retrieved on Aug. 7, 2019] Retrieved from Internet: URL<https://en.vexim.com/wp-content/uploads/sites/11/2017/03/SpineJack9%C2%AE-Surgical-Technique.pdf> ,12 pages.

* cited by examiner

KYPHOPLASTY SYSTEM AND METHOD

TECHNICAL FIELD

This document generally relates to kyphoplasty and/or other interventional spinal procedures.

BACKGROUND

Kyphoplasty is a minimally invasive surgical procedure for treatment of pain caused by vertebral body compression fractures. Typically, the procedure involves insertion of one or more coaxial 8-10 gauge bone introducer needles under fluoroscopic guidance into one or more fractured vertebral bodies utilizing a bipedicular, unipedicular, or extrapedicular approach. In some approaches, after a bone introducer needle is in place, the inner portion of the bone introducer needle is removed and the outer portion of the bone introducer needle remains as a guide and support for the remaining procedure. Through the bone introducer needle, a drill and curette are utilized for cavity creation in the vertebral body. In many cases, after the cavity is created, the drill and curette are removed, and a deflated balloon is inserted into the cavity of the vertebral body. The balloon is then inflated, for example, by injecting a solution into the balloon, thereby expanding the drilled cavity into a desired size within the vertebral body. When the cavity is expanded to the desired size, the balloon is deflated and removed from the vertebral body. Usually in such cases, a bone filler is advanced into the vertebral body, and the expanded cavity is filled with cement.

SUMMARY

Some embodiments described herein include a kyphoplasty system configured to simplify cavity creation and filling processes and to achieve rapid detachment of an implant after injection of filler material into a fractured vertebral body. For example, the kyphoplasty system can include a balloon implant that maintains a desired anatomic height (e.g., after a balloon is inserted to expand a vertebral body to a desired height) before and during the delivery of cement to the expanded cavity, and the balloon implant can be advantageously detached from a delivery shaft after delivery of cement to the expanded vertebral body. Further, in some examples described herein, the kyphoplasty system can employ an inflation plunger that can be coaxial within the delivery shaft and the balloon implant. The inflation plunger is configured to both deliver inflation fluid into the balloon implant to expand the vertebral body and also facilitate the detachment of the balloon implant from a cannula instrument after delivery of cement through the balloon implant and into the expanded vertebral body. Optionally, the inflation plunger can be provided in the form of an inflation plunger that is a coaxial elongate instrument that is withdrawable from the vertebral body contemporaneously with the withdrawal of the delivery shaft from the vertebral body (after detachment from the balloon implant that remains in the vertebral body).

Embodiments of the balloon implant disclosed herein integrate a balloon implant with a bone filler device. Some such embodiments are configured as a single unit which can be detachably coupled to a distal end of a delivery shaft of a kyphoplasty device. The balloon implant can be introduced into a fractured vertebral body by advancing the delivery shaft of the kyphoplasty device, with the balloon implant coupled at the distal end, into the fractured vertebral body. The delivery shaft with the balloon implant can be inserted into the vertebral body through, for example, a bone introducer needle or sheath. While inserted into the vertebral body, the balloon implant then advantageously allows both inflating the balloon implant and injecting bone filling substance into the fractured vertebral body. Such balloon implant inflation and bone filler injection can be performed sequentially, simultaneously, or alternatingly while the balloon implant remains in the vertebral body.

The balloon implant can be configured to form various inflated shapes, such as spheres, cylinders, cubes, diamonds, prisms, and other multifaceted 3-D shapes. For example, multifaceted shapes, such as diamond shapes, can increase surface area contact. In addition or alternatively, the kyphoplasty systems described herein can include multiple sets of delivery shafts and dual port devices that are operated simultaneously or in sequence.

Some embodiments of the technologies described herein include an improved detachment mechanism that can advantageously provide compact, secure, and reliable engagement between the delivery shaft and the balloon implant during the cavity creation and filling processes, but then can provide rapid and convenient detachment of the balloon implant structure during withdrawal of the delivery shaft away from the vertebral body. For example, the detachment mechanism can be sized sufficiently small while also providing a high-strength connection between a delivery cannula and the balloon implant structure (e.g., during relatively high injection pressures of bone cement passing through the balloon implant structure and into the vertebral cavity). As detailed below, the detachment mechanism can employ a coaxial arrangement of mating parts so as to remain in a position that avoids interfering with different instruments, inflation material, and bone cement material that may be introduced in a path toward the balloon implant. In some of these implementations, multiple instruments may be used in a small area of the patient body at the same time while also reducing obstructions in the working space located exterior to the patient.

Some embodiments of the technologies described herein include a detachment mechanism that reliably secures the balloon implant and its delivery shaft together. The detachment mechanism secures the balloon implant to the delivery shaft during injection of bone filler at relatively high pressures. In some examples, the balloon implant can include a threaded proximal end that releasably connects the balloon implant to its delivery shaft. The threaded connection between the balloon implant and the delivery shaft advantageously secures the balloon implant and the delivery shaft to each other at relatively high pressures of bone filler injection. Clinicians can easily detach the balloon implant from its delivery shaft by rotating the delivery shaft while securing the balloon implant from rotation to remove the delivery shaft from engagement with the balloon implant.

Some embodiments described herein include a kyphoplasty system. The kyphoplasty system can include a balloon implant member and a balloon member delivery shaft detachably connected to the balloon implant member. The balloon implant member may include a balloon coaxially mounted on a balloon shaft so that the balloon shaft provides at least one balloon inflation port into an interior of the balloon, the balloon implant member including a notch that extends longitudinally through a portion of threads at a proximal end of the balloon implant member. The balloon member delivery shaft can be detachably connected to the balloon implant member via a threaded connection to the threads such that central lumens of the balloon member delivery shaft and the balloon shaft are axially aligned. Optionally, the kyphoplasty system may include an inflation plunger defining an injection lumen and configured to slidingly advance through the central lumens of the balloon member delivery shaft and the balloon shaft to provide alignment of an exterior tab of the inflation plunger with the notch at the proximal end of the balloon implant member and to provide alignment of an inflation plunger aperture of the inflation plunger with the at least one balloon inflation port of the balloon implant member to inflate the balloon.

Such a kyphoplasty system may optionally include one or more of the following features. In some options, the inflation plunger aperture can be positioned along a circumferential surface of a distal end portion of the inflation plunger so that an inflation medium delivered through the injection lumen is output into the interior of the balloon. The exterior tab may be positioned relative to the inflation plunger aperture along the inflation plunger so that, when the exterior tab mates with the notch, the inflation plunger aperture aligns with the balloon inflation port. Also, a distal end of the balloon member delivery shaft can include internal threads that are configured to releasably mate with the threads at the proximal end of the balloon implant member. The balloon implant member may include at least one valve arranged proximate to the at least one balloon inflation port to allow flow of the inflation medium to inflate the balloon and to prevent an inflation medium from exiting the balloon. The valve can include at least one of a one-way flap valve or a one-way sleeve valve. In some options, the exterior tab can extend through the notch when the balloon implant member is releasably attached to a distal end portion of the balloon member delivery shaft. The exterior tab can engage with the notch to prevent rotation of the balloon implant member during rotation of the balloon member delivery shaft relative to the balloon implant member. Further, at least one of the balloon member delivery shaft, the balloon implant member, and the inflation plunger may include markings configured to facilitate alignment of the balloon implant member, the balloon member delivery shaft, and the inflation plunger. The kyphoplasty system may optionally include an injection needle defining an injection needle lumen and an injection needle tab, and the injection needle can be configured to slidingly advance through the central lumen of the balloon member delivery shaft to provide alignment of the injection needle tab with the notch at the proximal end of the balloon implant member.

Some embodiments described herein include a method for performing a kyphoplasty procedure. The method can include inserting a balloon implant member may include a balloon mounted on a balloon shaft into a vertebral body. The balloon implant member may be releasably attached to a distal end portion of a balloon implant delivery shaft via a threaded connection such that a lumen defined by the balloon implant delivery shaft and a lumen defined by the balloon shaft adjoin to define a first lumen. The method can also include inflating the balloon by injecting an inflation medium into a second lumen defined by an inflation plunger that is within the first lumen. The inflation plunger may optionally include an inflation aperture that aligns with one or more balloon shaft apertures. The method may include engaging a tab of the inflation plunger with a notch that extends through the threads of the balloon implant member. The method may also include securing a proximal end of the inflation plunger from rotation, and rotating the balloon implant delivery shaft in relation to the balloon implant member to release the threaded connection between the balloon implant member and the balloon implant delivery shaft.

Such a method for performing a kyphoplasty procedure may optionally include one or more of the following features or steps. The method may include, prior to inserting the balloon implant member into the vertebral body, advancing a bone introducer needle into the vertebral body, where the balloon implant member is inserted into the vertebral body through the bone introducer needle. The method may include, after advancing the bone introducer needle into the vertebral body and before inserting the balloon implant member into the vertebral body, advancing a space-making balloon through the bone introducer needle and inflating the space-making balloon within the vertebral body. The method may include, after inflating the balloon, retracting the inflation plunger from the first lumen. The method may include, after retracting the inflation plunger from the first lumen, inserting an injection needle through the first lumen and to a position distally of the distal opening of the balloon implant lumen, into the vertebral body. The method may include injecting filler material into the vertebral body external to the balloon implant member. The filler material can be injected into the vertebral body external to the balloon implant member via the injection needle. The method may include, after inflating the balloon, detaching the balloon implant member from the balloon implant delivery shaft such that the balloon implant member remains in the vertebral body. The method may include, after rotating the balloon implant delivery shaft in relation to the balloon implant member, detaching and retracting the balloon implant delivery shaft from the balloon implant member while leaving the balloon implant member in the vertebral body. The method may include, after detaching and retracting the balloon implant delivery shaft, detaching and retracting the inflation plunger from the balloon implant member while leaving the balloon implant member in the vertebral body.

The apparatuses, systems, devices, and techniques described herein may provide one or more of the following advantages. Some embodiments described herein include a kyphoplasty system that includes a balloon implant providing both balloon inflation and bone filling functionalities together in a single unit, thereby simplifying a kyphoplasty procedure. The dual port device improves height restoration of a fractured vertebral body by the balloon inflation, and permits for the vertebral body to be filled with the bone filler without losing the restored height.

Further, some embodiments described herein include a detachment mechanism between the balloon implant and its delivery shaft that secures the balloon implant to the delivery shaft during injection of bone filler at relatively high pressures. For example, in some embodiments the balloon implant can include a threaded proximal end that releasably connects the balloon implant to its delivery shaft. The threaded connection between the balloon implant and the delivery shaft are advantageously secure at relatively high pressures of bone filler injection, as well as easy and intuitive to use. That is, clinicians can easily detach the balloon implant from its delivery shaft by rotating the delivery shaft while securing the balloon implant from rotation to remove the delivery shaft from engagement with the balloon implant.

Moreover, some embodiments described herein include an inflation plunger that is used to deliver a balloon inflation medium to enlarge the balloon implant. As described further below, the design and functionality of the inflation plunger advantageously aligns a delivery opening of the inflation plunger with one or more apertures that provide fluid communication between the lumen of the balloon implant member and the interior of the balloon. The inflation plunger advantageously aligns the delivery opening with the one or more apertures while engaging a notch of the balloon implant. Engagement between the inflation plunger and the notch of the balloon implant allows a clinician to easily secure the balloon implant from rotation while rotating the delivery shaft to remove the delivery shaft from engagement with the balloon implant.

The details of one or more implementations are set forth in the accompanying drawings and the description below. Other features and advantages will be apparent from the description and drawings, and from the claims.

DETAILED DESCRIPTION OF ILLUSTRATIVE EMBODIMENTS

Figure 1:
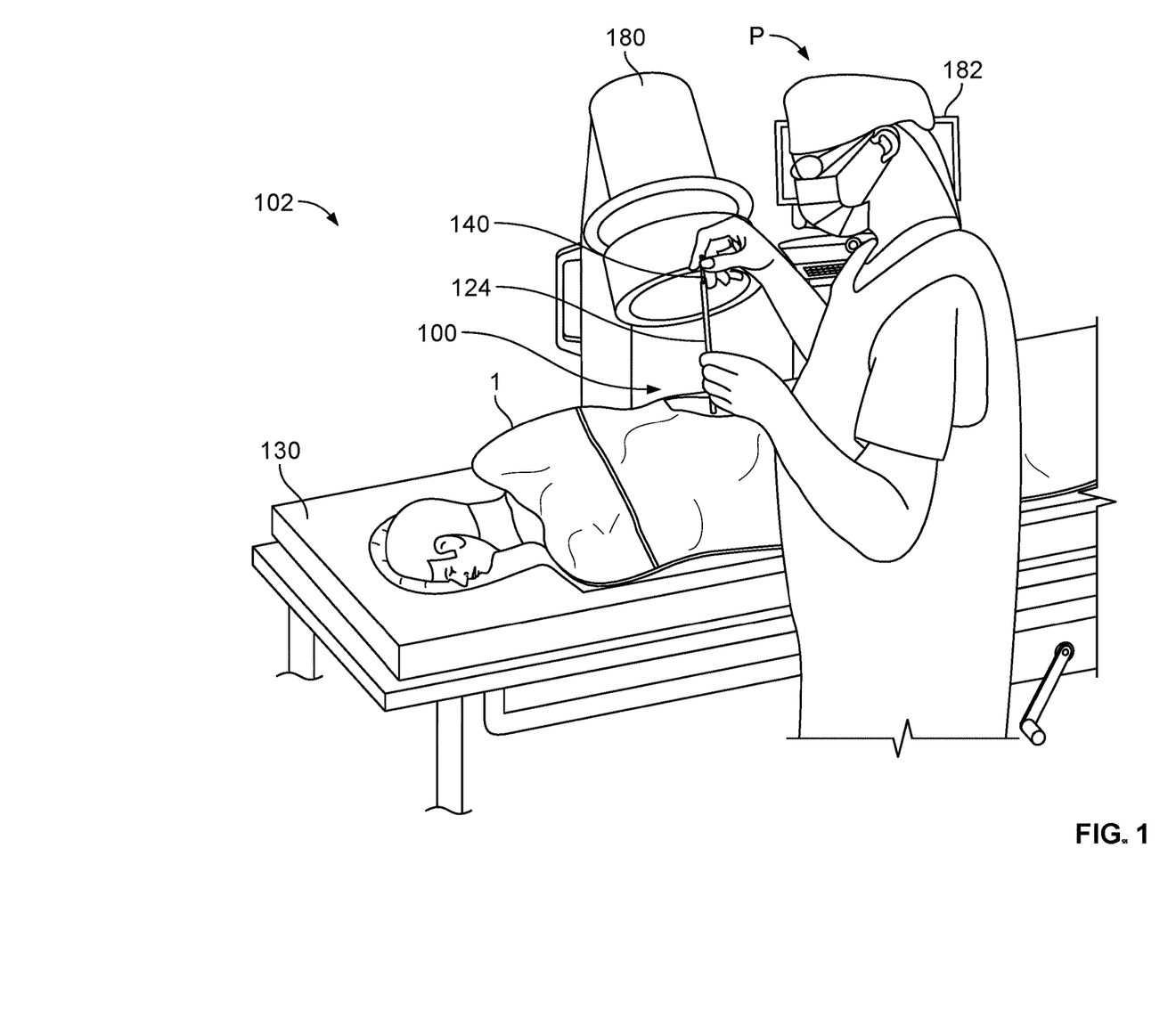
FIG. 1 depicts the clinical use of an example kyphoplasty system, in accordance with some embodiments described herein.
Figure 2:
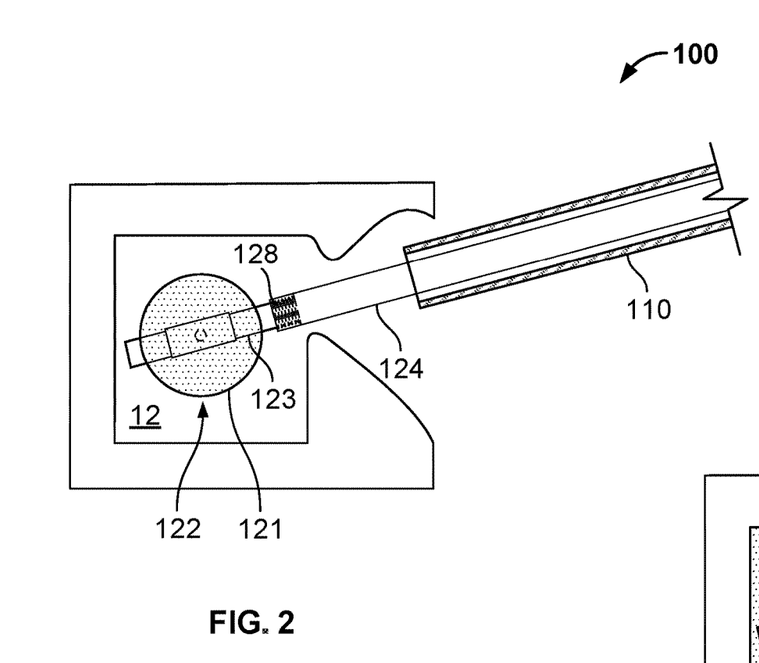
FIGS. 2-3 schematically illustrate the implantation of an example kyphoplasty apparatus to restore a fractured vertebral body, for example, using the system of FIG. 1.
Figure 3:
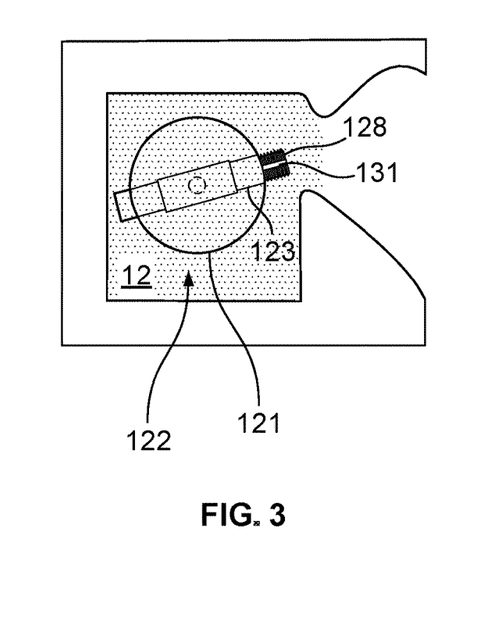

Referring to FIG. 1, some embodiments of a kyphoplasty system 100 can be used by a practitioner P to perform a kyphoplasty procedure in a surgical theater 102. In the depicted embodiment, the system 100 can include a delivery shaft 124 that is detachably connected to a balloon implant (FIGS. 2-3) and an inflation plunger 140 that is configured to slide coaxially within the delivery shaft 124. In some embodiments, both the delivery shaft 124 and the inflation plunger 140 can be manipulated by the practitioner P while the patient 1 is laying prone on a prone table mat 130 during the kyphoplasty procedure. In some examples, both the delivery shaft 124 and the inflation plunger 140 can be manipulated by the practitioner P while the patient 1 is laying in a prone position during the kyphoplasty procedure. In some implementations detailed below, the delivery shaft 124 and the inflation plunger 140 can move relative to one another in order to advantageously detach the balloon implant from the delivery shaft 124 after delivery of cement to the expanded vertebral body (FIGS. 2-3).

In the surgical theater 102, the kyphoplasty system 100 can be used in conjunction with an image scanner 180, such as a C-arm fluoroscopy machine, and a display device 182 configured to receive images (e.g., still and/or video images) from the image scanner 180 and to display the images to assist a practitioner P with visualization during the kyphoplasty procedure. In some embodiments, one or more components of the kyphoplasty system 100 can include one or more radiopaque markers. For example, in some embodiments the kyphoplasty system 100 includes an implantable balloon member that can include one or more radiopaque markers.

While the kyphoplasty system 100 and procedure is described in greater detail below, briefly the kyphoplasty procedure in this example includes advancing a bone introducer needle toward a vertebral body of the patient 1. While the bone introducer needle is in place, the inner portion of the bone introducer needle is removed and the outer portion of the bone introducer needle remains as a guide and support for the remaining procedural steps.

Through the bone introducer needle, a drill and curette may be utilized for cavity creation in the vertebral body. In many cases, after the cavity is created, the drill and curette are removed, a high pressure balloon can be inserted into the vertebral body and inflated to create a space in the vertebral body and then deflated and removed, and a deflated balloon implant is inserted into the vertebral body. The balloon implant is then inflated, for example, by injecting a solution or filler material (e.g., bone cement) into the balloon implant, thereby expanding the drilled cavity into a desired size within the vertebral body and thereby restoring the height of the vertebral body. When the vertebral body is expanded to the desired size by the inflated balloon implant, a bone filler (e.g., bone cement) is injected into the vertebral body to engage and fill the vertebral body trabecular bone around the inflated balloon implant. When the expanded cavity is sufficiently filled with the bone filler material, the balloon implant is then detached and left within the restored vertebral body, and the other components of the kyphoplasty system 100 are retracted from the patient 1. In some embodiments, to detach the balloon implant, the practitioner P rotates an outer sheath of a delivery shaft 124 while holding an inflation plunger 140. The inflation plunger 140 engages with the balloon implant to prevent the balloon implant from rotation with the delivery shaft 124. The independent rotation of the delivery shaft 124 from the balloon implant allows the practitioner P to detach the balloon implant and leave the balloon implant within the restored vertebral body, and the other components of the kyphoplasty system 100 are retracted from the patient 1.

Referring now to FIGS. 2-3, some embodiments of the kyphoplasty system 100 include the balloon implant 122 that can be advantageously detached from the delivery shaft 124 after bone cement is injected through the delivery shaft 124 after delivery of cement to the expanded vertebral body and into the expanded vertebral body 12. In doing so, the both the delivery shaft 124 and the inflation plunger 140 can be withdrawn from the vertebral body 12 while the balloon implant 122 remains within the vertebral body with the bone cement material. The kyphoplasty system 100 includes a balloon implant member 122 that is advanced into the vertebral body 12 via an introducer needle 110 (shown in longitudinal cross-section).

The balloon implant member 122 can be configured as an expandable implant structure that is in a collapsed state during insertion into the vertebral body 12, expands to an expanded state within the vertebral cavity 12, and then remains positioned within the vertebral body 12 after delivery of bone cement material into vertebral cavity 12. The balloon implant member 122 is releasably attached to the balloon member delivery shaft 124, which as detailed below, can include an improved detachment mechanism that maintains the implant member 122 in a stationary position relative to the delivery shaft 124 (and, optionally, also stationary within the vertebral body 12) during the disconnection process. For example, the balloon implant member 122 has exterior threads 128 at the proximal end of central coaxial shaft 123 of the balloon implant member 122 that mate with corresponding interior threads at the distal end of the balloon member delivery shaft 124. The threaded connection between the balloon implant member 122 and the balloon member delivery shaft 124 provides a reliable and secure connection between the components during kyphoplasty procedures, including during injection of the bone filler material (described below). As described further below, an inflation plunger extends through the lumen of the balloon member delivery shaft 124, and the inflation plunger is used to deliver bone filler material (e.g., bone cement) into the balloon implant 122. Optionally, filling the balloon implant 122 can beneficially cause the fractured vertebral body 12 to be restored to a desired height or expanded condition. Subsequent to expanding the balloon implant member 122 with the bone filler material, in some embodiments, an injection needle extends through the lumen of the balloon member delivery shaft 124 (see e.g., FIG. 12) for purposes of delivering bone filler material (e.g., bone cement) through the central coaxial shaft 123 of the balloon implant member 122 and into the vertebral body 12 (thereby providing the bone filler material external to the expanded balloon implant member 122).

As schematically depicted in FIG. 3, after the bone filler material is injected into the balloon implant 122 and into the vertebral body 12, the balloon member delivery shaft 124 can be detached from the balloon implant member 122 for withdrawal of delivery shaft 124 (while the balloon implant member 122 remains implanted within the vertebral body 12). In some embodiments, to detach the balloon implant member 122, the delivery shaft 124 is rotated about its central axis relative to the balloon implant member 122 so as to unthread the delivery shaft 124 from the threads 128 at the proximal end of the balloon implant member 122. As described in more detail below, the detachment mechanism can also include an elongate coaxial instrument (e.g., the inflation plunger 140 described in further detail below) that engages with the balloon implant member 122 to maintain the balloon implant member 122 in a substantially stationary position during rotation of the delivery shaft 124. The independent rotation of the delivery shaft 124 from the balloon implant member 122 allows detachment of the balloon implant member 122 from the delivery shaft 124. The balloon implant member 122 is left implanted within the restored vertebral body 12. While in the depicted scenario a single balloon implant member 122 is implanted within the restored vertebral body 12, in some cases two balloon implant members 122 are implanted within the restored vertebral body 12 with each balloon implant members 122 being detachably connected to a respective delivery shaft 124.

Figure 4:
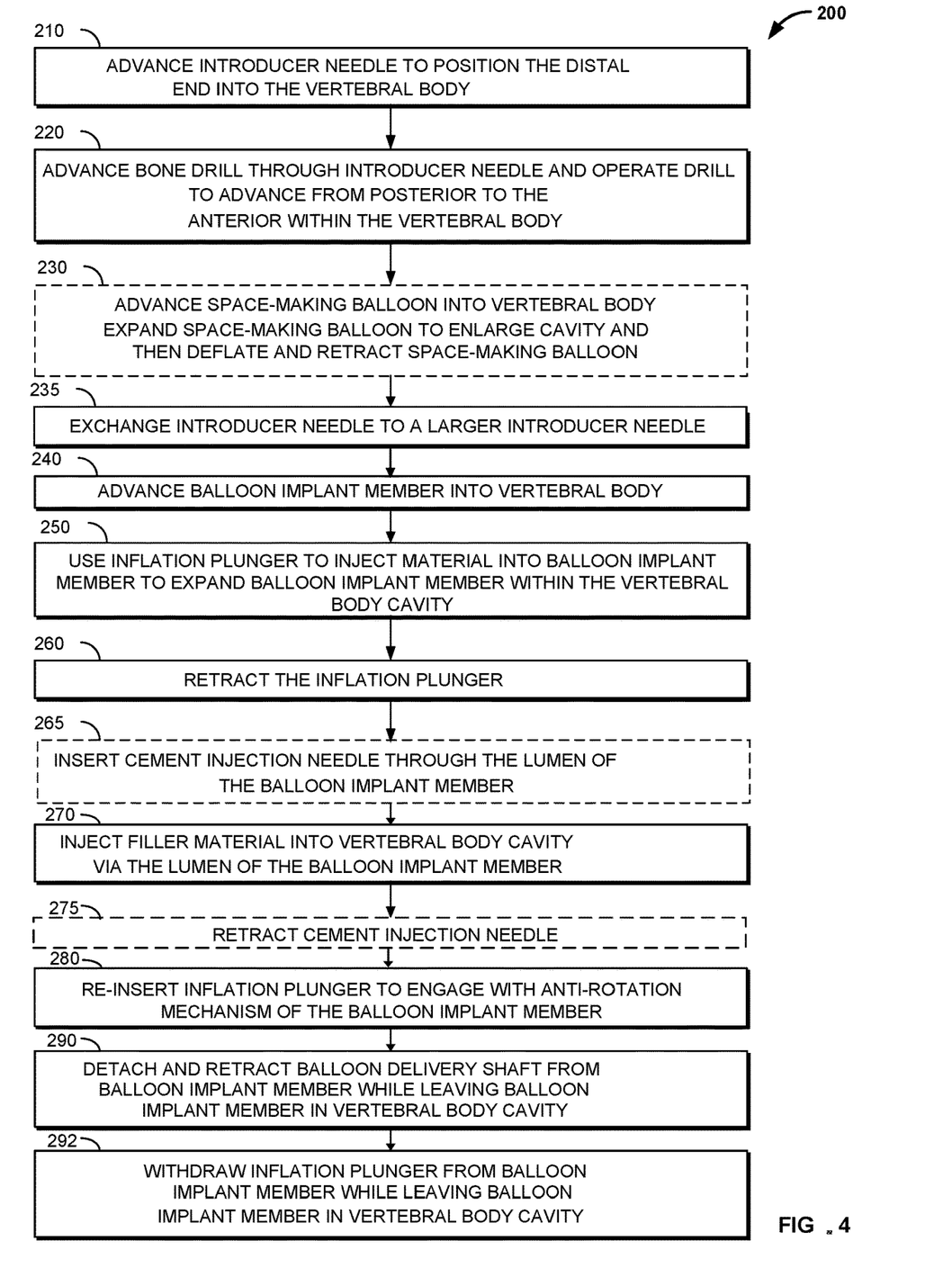
FIG. 4 is a flowchart that describes an example kyphoplasty method in accordance with some embodiments.
Figure 5A:
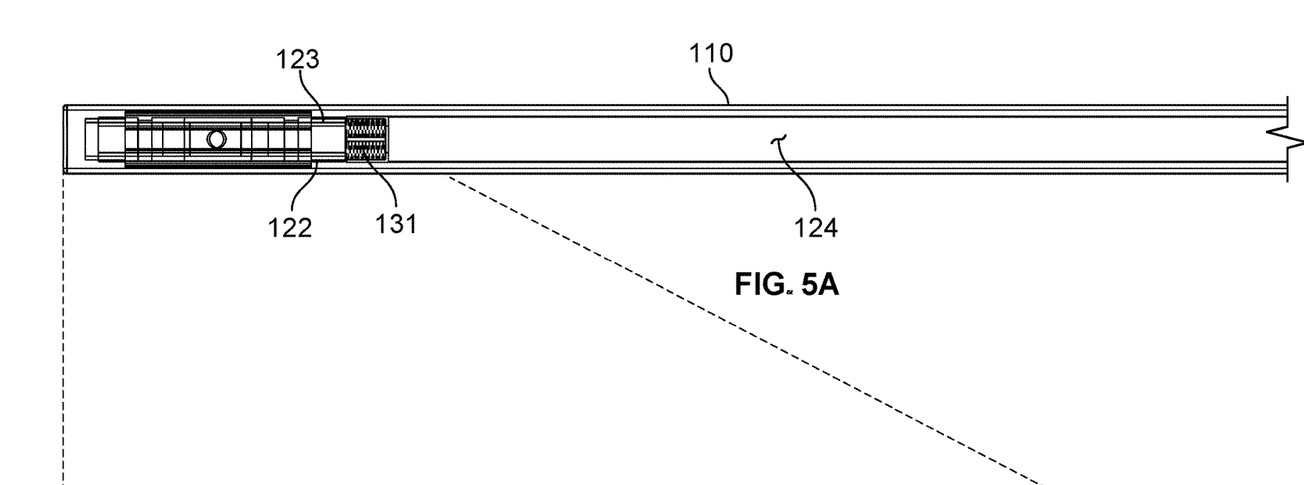
FIG. 5A illustrates an example kyphoplasty system in a delivery configuration.
Figure 5B:
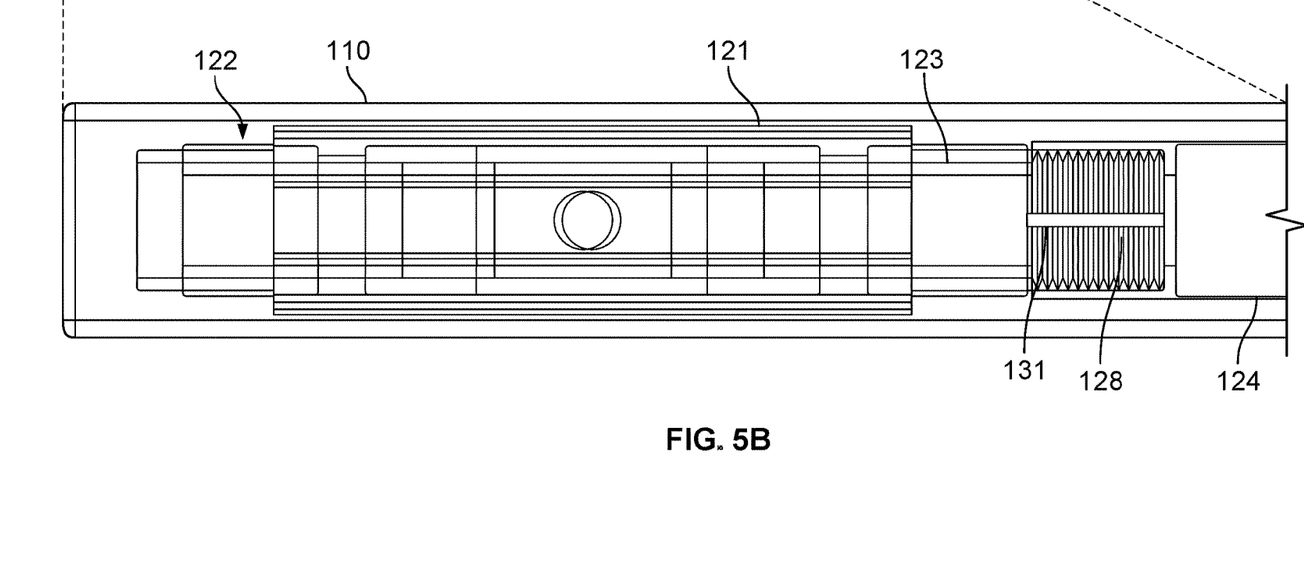
FIG. 5B is a close-up view of a distal end portion of the kyphoplasty system of FIG. 5A.

Referring now to FIG. 4, some implementations of an example balloon kyphoplasty process 200 can use the above-described system 100 to treat a fractured vertebra. The process 200 can include a step 210, in which a bone introducer needle (which can also be referred to as a sheath or trocar) is advanced into the fractured vertebra of the patient under x-ray fluoroscopy guidance. The bone introducer needle is advanced to position the distal end of the introducer needle into the vertebral body (e.g., at a posterior side of the vertebral body). The bone introducer needle defines a lumen through which various instruments of the kyphoplasty system 100, as described further below, can be advanced to treat the fractured vertebral body of the patient. In some embodiments, the introducer needle includes a backflow prevention device configured to prevent backflow of blood or body fluids through the needle.

In step 220, a bone drill is advanced through the lumen of the introducer needle into the fractured vertebral body. The bone drill is then rotatably driven to advance the bone drill from the posterior to the anterior of the vertebral body and create an opening for placement of the balloon implant in the vertebral body. Afterwards, in some cases the introducer needle is then advanced farther, through the opening created by the bone drill. The bone drill can also be used to create an initial open void inside of the vertebral body. The bone drill can then be retracted and removed from the lumen of the introducer needle.

Optionally, at step 230, a high-pressure space-making balloon can be advanced through the lumen of the introducer needle and into the vertebral body. In some cases, the high-pressure space-making balloon can be configured to receive an inflation pressure of 300 psi to 1200 psi, 800 psi to 1100 psi, and about 1000 psi in particular embodiments. The space-making balloon can then be inflated. The inflation of the space-making balloon elevates the fractured vertebra to its pre-fracture height, and creates a larger void in the vertebral body. The space-making balloon can then be deflated. Then, the space-making balloon can be retracted and removed from the lumen of the introducer needle.

In step 235, the introducer needle can be exchanged with a larger introducer needle (e.g., an introducer needle with a larger needle gauge). For example, the introducer needle can be exchanged within the vertebral body, where a K-wire exchange is performed to a 6 gauge introducer needle (e.g., a 6 gauge reamer) to upsize the introducer needle to a 6 gauge size. The larger introducer needle is positioned in the posterior aspect of the vertebral body In step 240, a balloon implant of the kyphoplasty systems 100 described herein can be advanced through the lumen of the larger bone implant introducer needle (e.g., the 6G reamer from step 235) and into the vertebral body. For example, the balloon implant can be in the form of the balloon implant member 122 described herein, which may include the improved detachment mechanism that releasably connects the balloon implant member 122 to the delivery shaft 124 during advancement into the vertebral body. During the advancement in step 240, the balloon member of the balloon implant can be maintained in a collapsed state to provide a low-profile delivery configuration. The balloon implant can be advanced so that a distal portion of the balloon implant is within the anterior aspect of the vertebral body.

For example, referring now to FIGS. 5A-5B and 6A-6B for an illustrative example of the assembly that can be employed in step 240 (FIG. 4), the example balloon implant member 122 of the kyphoplasty systems 100 is depicted in a collapsed state within a lumen of an introducer needle 110 (shown transparently). In this embodiment, the kyphoplasty system 100 includes the balloon implant member 122 and the balloon member delivery shaft 124, both of which are configured for advancement into the introducer needle 110. The balloon implant member 122 is releasably coupled to a distal end portion of the balloon member delivery shaft 124. As described further below, the detachment mechanism can employ the exterior threads 128 to releasably couple the balloon implant member 122 to the balloon member delivery shaft 124 in a manner that provides sufficient strength (e.g., to resist separation forces between the implant member 122 and the delivery shaft 124 during injection of bone filler material) and in a manner that maintains the open path along the central axis of implant member 122 and delivery shaft 124. For example, the balloon implant member 122 and the balloon member delivery shaft 124 each define a lumen. While the balloon implant member 122 is releasably coupled to the balloon member delivery shaft 124, the lumens of the balloon implant member 122 and the balloon member delivery shaft 124 are adjoining so as to function as a single lumen when the balloon implant member 122 and the balloon member delivery shaft 124 are connected to each other.

Figure 6A:
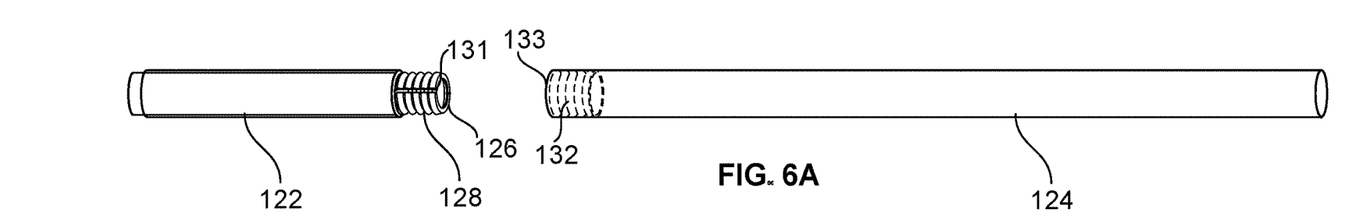
FIG. 6A illustrates an example balloon implant device separated from an example balloon implant delivery shaft.
Figure 6B:
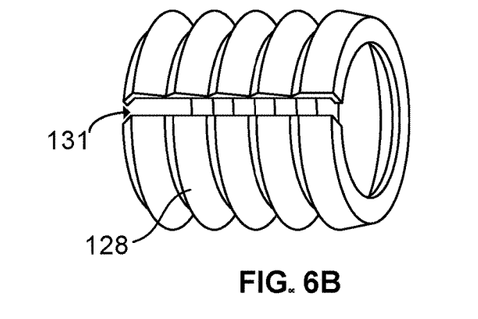
FIG. 6B is a close-up view of a proximal end portion of the balloon implant device of FIG. 6A.

As shown in FIGS. 6A and 6B, the detachment mechanism of the balloon implant member 122 can include the thread structure 128 having a longitudinal slot therein to provide a mating notch 131 for engagement with another instrument (described below). As previously described, the threads 128 are positioned at a proximal end 126 of a coaxial balloon shaft 123 of the balloon implant member 122, and the threads 128 are oriented to mate with corresponding threads 132 at the distal end 133 of the balloon member delivery shaft 124. In this example, the threads 132 are positioned on an interior (e.g., lumen side) of the balloon member delivery shaft 124 at the distal end 133. As such, the threads 128 of the balloon implant member 122 can be received within the distal end 133 of the balloon member delivery shaft 124 by engaging the threads 128 with the threads 132. The threaded connection between the balloon implant member 122 and the balloon member delivery shaft 124 advantageously secures the balloon implant member 122 and balloon member delivery shaft 124 to each other. The threaded connection can be configured to provide sufficiently high strength resistance to separation forces during injection of the bone filler (e.g., bone cement) at relatively high pressures, thereby maintaining a stable and secure connection between the balloon implant member 122 and the balloon member delivery shaft 124 at this phase of the procedure. For example, the high strength resistance to separation forces during injection of the bone filler (e.g., bone cement) at relatively high pressures such as from 100 psi to 300 psi, from 150 psi to 250 psi, or about 200 psi in some embodiments.

Figure 7A:
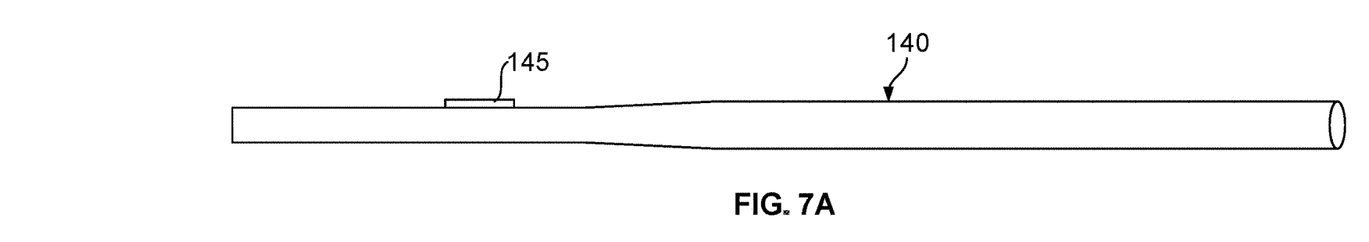
FIG. 7A illustrates a side view of an example inflation plunger component of the kyphoplasty systems described herein.
Figure 7B:
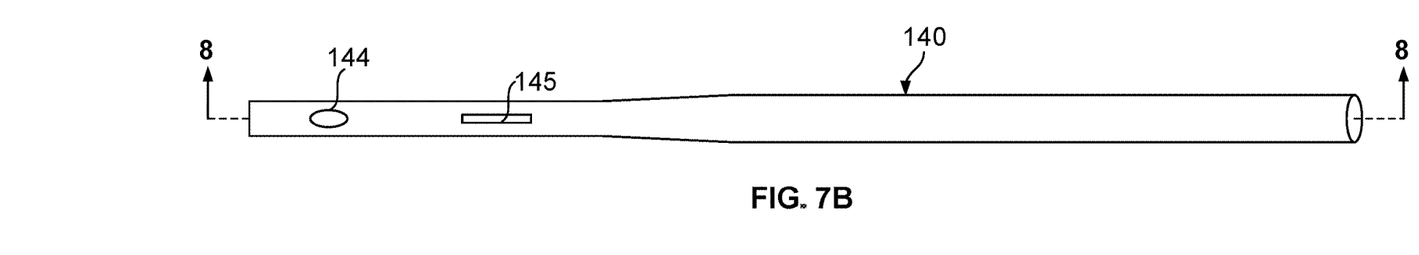
FIG. 7B illustrates a top view of the inflation plunger of FIG. 7A.

The mating notch 131 extends from the proximal end 126 of the balloon implant member 122 for an axial length in a distal direction toward the expandable balloon (but, in this embodiment, to fully to the balloon). For example, the notch 131 can extend through the thickness of the circumferential wall of the central shaft 123 and extend for the same axial length as the threads 128. As such, the notch 131 creates a slot through at least a portion of the threads 128, which as described in detail below, can be configured to matingly receive a tab 145 of the inflation plunger 140 (FIGS. 7A-7B). In this embodiment, the notch 131 creates an opening in a portion of the threads 128, and both the exterior threads 128 and the mating interior threads 132 do not fully occupy the space of the notch 31 when the balloon implant member 122 and the balloon member delivery shaft 124 are connected to each other via the threads 128 and the threads 132 (thereby providing access to the notch 131 for slidably receiving the tab 145 both when the exterior threads 128 and the interior threads 132 are mated and when the exterior threads 128 and the interior threads 132 are separated).

Referring again to FIG. 4, the process 200 can include step 250 in which the balloon implant is expanded, for example, to restore the vertebral body to a selected height or size. In this embodiment, the system 100 can employ an inflation plunger that is slidably advanced into in the coaxial lumens of the balloon implant member 122 and the balloon member delivery shaft 124 to a selected position so that the inflation plunger can direct bone filler material (e.g., bone cement) into the interior space of the expandable balloon, thereby inflating the balloon implant member 122 with bone filler material (e.g., bone cement). This inflation of the balloon implant member 122 is executed while the balloon implant member 122 is located in the vertebral body.

For example, referring now to FIGS. 7A-7B and 8-11 for an illustrative example of the assembly that can be employed in step 250 (FIG. 4), the inflation plunger 140 can be in the form on an elongate instrument having a shaft 142 that slidably inserts through the lumen of the delivery shaft 124. A distal end portion of the shaft 142 defines one or more inflation apertures 144. The inflation apertures 144 are openings to a central lumen 143 of the inflation plunger 140. In this example, one inflation aperture 144 is included in the inflation plunger 140. The shaft 142 has a tapered region 146 such that an outer diameter of the shaft 142 at its distal end is smaller than an outer diameter of the shaft 142 at its proximal end, and the tab 145 is positioned distally of the tapered region 146 (e.g., along a portion of the shaft 142 having the smaller diameter). The tab 145 that extends outwardly from the shaft 142 to an exterior height so that the outermost lateral edge of the tab 145 is no further from the central axis of the shaft 142 than the larger outer diameter of the shaft 142 (e.g., at the proximal end of the shaft 142). That way, the tab 145 protrudes from the shaft 142, but does not interfere with the plunger 140 being slidably inserted and withdrawn from the delivery shaft 124. In some embodiments, the tab 145 has a rectangular shape that extends along an outer portion of the shaft 142. The tab 145 can be positioned proximally from the inflation aperture 144, where the inflation aperture 144 is positioned between a distal end 153 of the inflation plunger 140 and the tab 145. The tab 145 is configured to be inserted in the notch 131 of the balloon implant member 122 (e.g., via an interference fit, a keyed connection, or otherwise inserted in and received by the notch 131). In this embodiment depicted in FIGS. 7A-7B and 8, the tab 145 and the inflation aperture 144 are aligned with each other in the same central longitudinal plane of the inflation plunger 140 extending along a central axis of the shaft 142. For example, the tab 145 and the inflation aperture 144 have a position around the outer portion of the shaft 142 that is approximately equal with each other so that the tab 145 and the inflation aperture 144 are aligned with each other. In some embodiments, alignment of the tab 145 and the inflation aperture 144 facilitates a connection between the tab 145 and the notch 131 while the inflation aperture 144 is aligned with one or more apertures 127 of the balloon shaft 124. As stated above, the inflation plunger 140 is sized to slidably advance into the coaxial lumens of the balloon implant member 122 and the balloon member delivery shaft 124.

Figure 9:
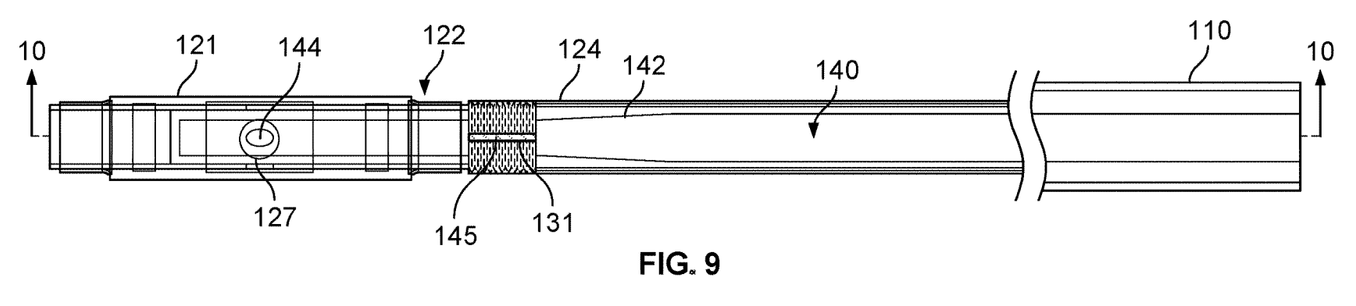
FIG. 9 illustrates the kyphoplasty system of FIG. 5A with an inflation plunger inserted.
Figure 10:
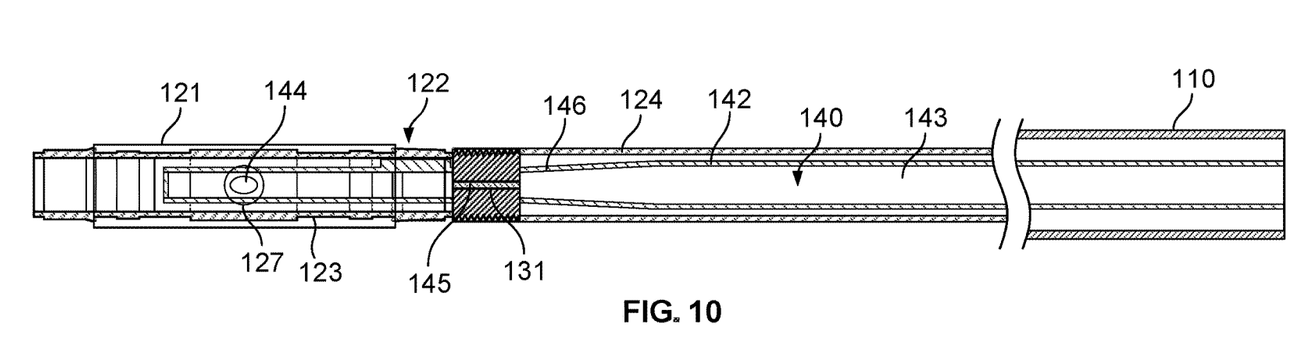
FIG. 10 is a longitudinal cross-section view of the kyphoplasty system of FIG. 9.

For example, as shown in FIGS. 9-10, the inflation plunger 140 can be slidably inserted into the lumens of the balloon implant member 122 and the balloon member delivery shaft 124 so that the inflation aperture 144 is aligned with a corresponding inflation port of the balloon implant member 122. As shown in FIGS. 9-10, the balloon implant member 122 is not yet inflated in this arrangement. The inflation plunger 140 is advanced through the lumens of the implant member 122 and the balloon member delivery shaft 124 so that the tab 145 engages with and is received in the notch 131 and so that the inflation aperture 144 is aligned with the one or more apertures 127 of the balloon shaft 124. In this aligned configuration, the bone filler material (e.g., bone cement) can be injected through the inflation plunger 140 and into the balloon implant member 122 for purposes of expanding the balloon within the vertebral body.

In some embodiments, the tapered region 146 of the shaft 142 tapers so that an outer diameter of the shaft 142 at a distal end 147 of the shaft 142 is smaller than an outer diameter of the shaft 142 at a proximal end of the shaft 140. In this embodiment, the gentle taper to the tapered region 146 of the inflation plunger 140 matches a gentle taper to the balloon shaft 123 of the balloon implant 122, and the matching tapering geometry of the inflation plunger 140 and the balloon implant member 122 (e.g., including the tapered region 146 and the diameter of the shaft 142 at the distal end 147 of the shaft 142, and the diameter of the balloon shaft 123), along with the viscosity of the bone filler material (e.g., bone cement) dispensed from the inflation plunger 140 can facilitate inflation of the balloon implant member 122 via alignment between the inflation aperture 144 and the one or more apertures 127 of the balloon implant member 122. The inflation of the balloon implant member 122 can occur such that, when bone filler material (e.g., bone cement) is injected through the inflation aperture 144 the filler material flows through the one or more apertures 127 of the balloon implant member 122 to inflate the balloon implant member 122. In some aspects, the alignment between the inflation aperture 144 and the one or more apertures 127 of the balloon implant member 122 and the matching tapering geometry of the inflation plunger 140 and the balloon implant member 122 can facilitate a seal-less connection between the inflation plunger 140 and the balloon implant member 122 while facilitating inflation of the balloon implant member 122. The seal-less connection between the inflation plunger 140 and the balloon implant member 122 occur without seals on the proximal and distal sides of the inflation aperture 144. Optionally, one or more ring seals can be implemented along the circumference of the inflation plunger 140 (e.g., a distal ring seal and a proximal ring seal on opposing sides of the inflation aperture 144.

In some embodiments, at least one of the balloon member delivery shaft 124, the balloon implant member 122, and the inflation plunger 140 includes markings configured to facilitate alignment of the balloon member delivery shaft 124, the balloon implant member 122, and the inflation plunger 140. The one or more markings can be external markings at least one of the balloon member delivery shaft 124, the balloon implant member 122, and the inflation plunger 140 so that the markings indications, symbols, emblems, or other indicators are visible to practitioner P (e.g., via visual inspection, via medical imaging, or otherwise seen be the practitioner P). For example, the inflation plunger 140 can include one or more markings, indications, symbols, emblems, or other indicators that represent and correspond to a rotational position of the inflation aperture 144 and the tab 145. In some embodiments, the one or more markings can be positioned at a proximal end of the inflation plunger 140 (e.g., outside of a proximal end of the balloon member delivery shaft 124) that is visible to practitioner P so that the practitioner P knows the rotational position of the inflation aperture 144 and the tab 145. The balloon implant member 122 can include one or more markings, indications, symbols, emblems, or other indicators that represent and correspond to a rotational position of the one or more apertures 127 and the notch 131. The balloon member delivery shaft 124 can include one or more markings, indications, symbols, emblems, or other indicators that represent and correspond to a rotational position of the notch 131 to facilitate alignment of the notch with the one or more markings. In some embodiments, each of the balloon member delivery shaft 124, the balloon implant member 122, and the inflation plunger 140 include the one or more markings. In some embodiments, any combination of markings may be implemented. For example, the inflation plunger 140 can include one or more markings at the proximal end of the inflation plunger 140 and the balloon implant member can include markings that that represent and correspond to a rotational position of the one or more apertures 127 and the notch 131.

Figure 11:
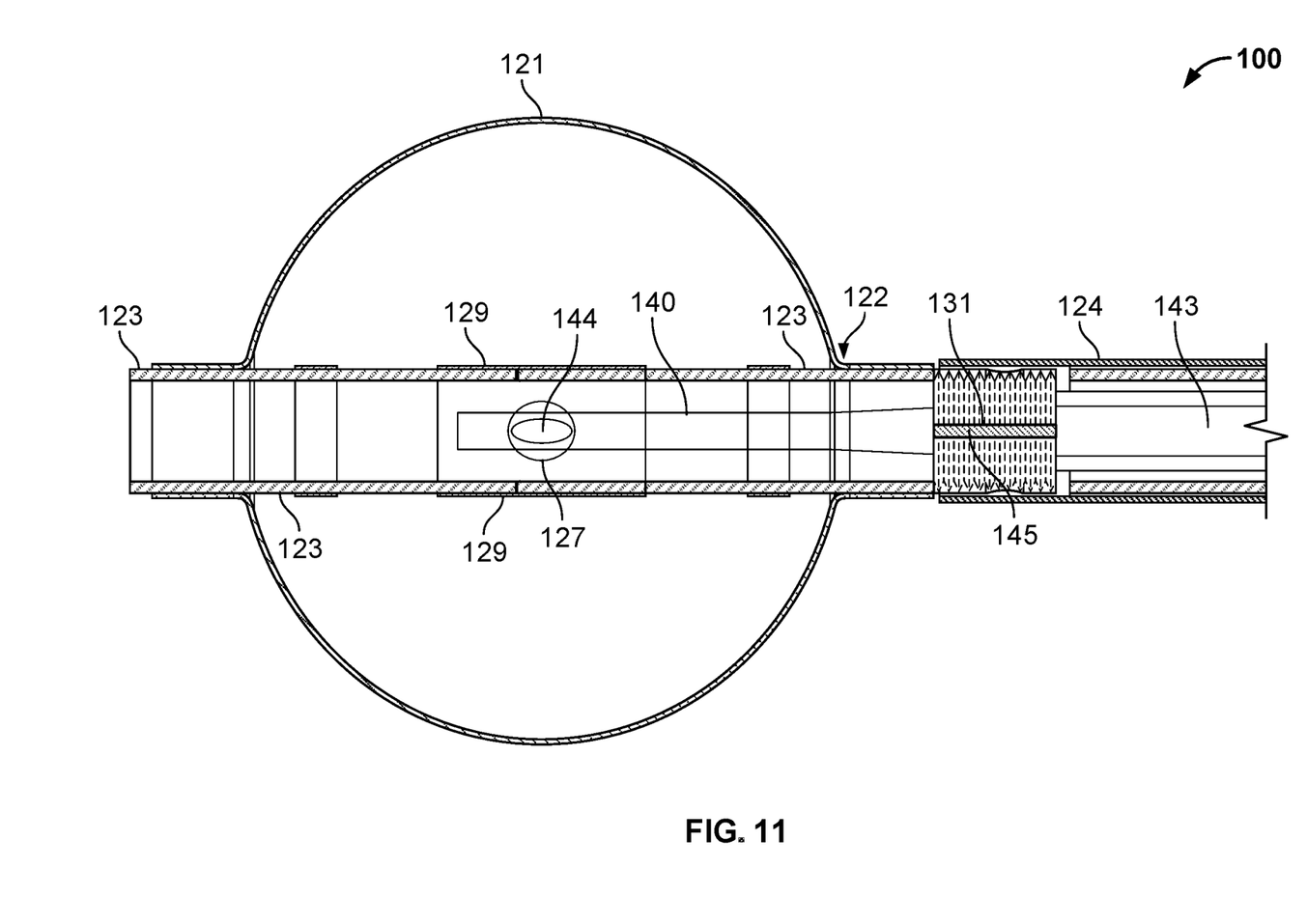
FIG. 11 illustrates the kyphoplasty system of FIG. 9 with the balloon member in an expanded configuration.

For example, as shown in FIGS. 10-11, the balloon implant member 122 includes a balloon 121 that is adjusted from a collapsed condition (FIG. 10) to an expanded condition (FIG. 11) due to the injection of an inflation medium into the balloon implant member 122 using the inflation plunger 140. This example depicts the expansion of the balloon implant member 122, as previously described in connection with step 250 of the process 200 (FIG. 4). In particular embodiments, the balloon implant member 122 includes the balloon 121 that is fixedly attached to the central balloon shaft 123. The balloon shaft 123 defines the lumen of the balloon implant member 122 that is aligned with the lumen of the balloon member delivery shaft 124. The balloon shaft 123 defines one or more apertures 127. The one or more apertures 127 provide fluid communication between the lumen of the inflation plunger 140 and the interior of the balloon 121 via the alignment between the one or more apertures 127 and the inflation aperture 144. Accordingly, inflation medium can pass from the inflation plunger 140 into the interior of the balloon 121 via the one or more apertures 127 of the balloon shaft 123.

Still referring to FIGS. 10-11, the balloon implant member 122 in this embodiment also includes one or more one-way valves 129. The one or more one-way valves 129 are positioned between the one or more apertures 127 and the interior of the balloon 121. Accordingly, the one or more one-way valves 129 allow flow of the inflation medium into the balloon 121 (to inflate the balloon 121), but prevent the flow of the inflation medium in the opposite direction. This means that the inflation medium that enters the interior of the balloon 121 stays in the interior of the balloon 121. In some embodiments, the one or more one-way valves 129 may be a sleeve made of a flexible material such as, but not limited to, silicone or urethane. Accordingly, the one or more one-way valves 129 may be referred to as sleeve valves. In some embodiments, the one or more one-way valves 129 may include displaceable flap members that open to allow flow into the interior of the balloon 121, and that close when the flow is stopped. Other types of one-way valves 129 can also be utilized.

Figure 8:
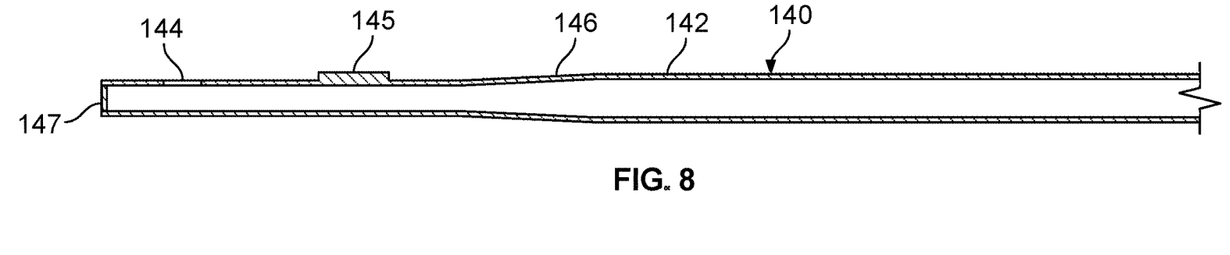
FIG. 8 is a longitudinal cross-section view of the inflation plunger of FIG. 7B.

As described in FIG. 4 (step 250) and in FIG. 11, the inflation medium can be injected by the practitioner P (FIG. 1) into the lumen 143 of the inflation plunger 140. In some cases, the balloon 121 is filled at an injection pressure of about 100 psi to about 250 psi, about 150 psi to about 250 psi, or preferably about 200 psi. In some cases, the inflation medium that is injected into the balloon 121 is a type of solidifying liquid such as orthopedic cement or bone cement (e.g., polymethyl methacrylate, calcium phosphate, magnesium phosphate, amorphous magnesium phosphate, etc.). In some cases, a contrast bone cement can be used as the inflation medium that is injected into the balloon 121. The inflation medium flows distally through the lumen 143 of the inflation plunger 140 and exits the inflation plunger 140 via the one or more apertures 144 (FIGS. 7 and 8). Accordingly, the balloon 121 is inflated as follows. The inflation medium is injected into the lumen 143 of the inflation plunger 140. The inflation medium flows distally in the lumen 143 of the inflation plunger 140 and exits the inflation plunger 140 via the one or more apertures 144 to enter the one or more apertures 127 of the balloon shaft 123. The inflation medium passes through the one or more one-way valves 129, and enters the interior of the balloon 121. This completes step 250 of the balloon kyphoplasty procedure 200 illustrated in FIG. 4.

Referring again to FIG. 4, the process 200 can include step 260 in which the inflation plunger 140 is retracted out of the lumens of the balloon shaft 123 and the balloon member delivery shaft 124. The lumens of the balloon shaft 123 and the balloon member delivery shaft 124 become unobstructed when the inflation plunger 140 is retracted, and in this embodiment, provide access along the central axis to a distal-facing port at the distal end of the balloon shaft 123.

In step 265 of the balloon kyphoplasty procedure 200 illustrated in FIG. 4, a cement injection needle is inserted through the lumen of the balloon implant. The injection needle can inject filler material (e.g., orthopedic cement as described above) into the vertebral body through the lumen of the kyphoplasty system 100. In some embodiments, the injection needle 150 is an elongate needle (e.g., a 13 gauge needle) configured to inject the filler material in a path along the central axis of the balloon shaft 123 to the distal-facing port at the distal end of the balloon shaft 123.

Figure 12:
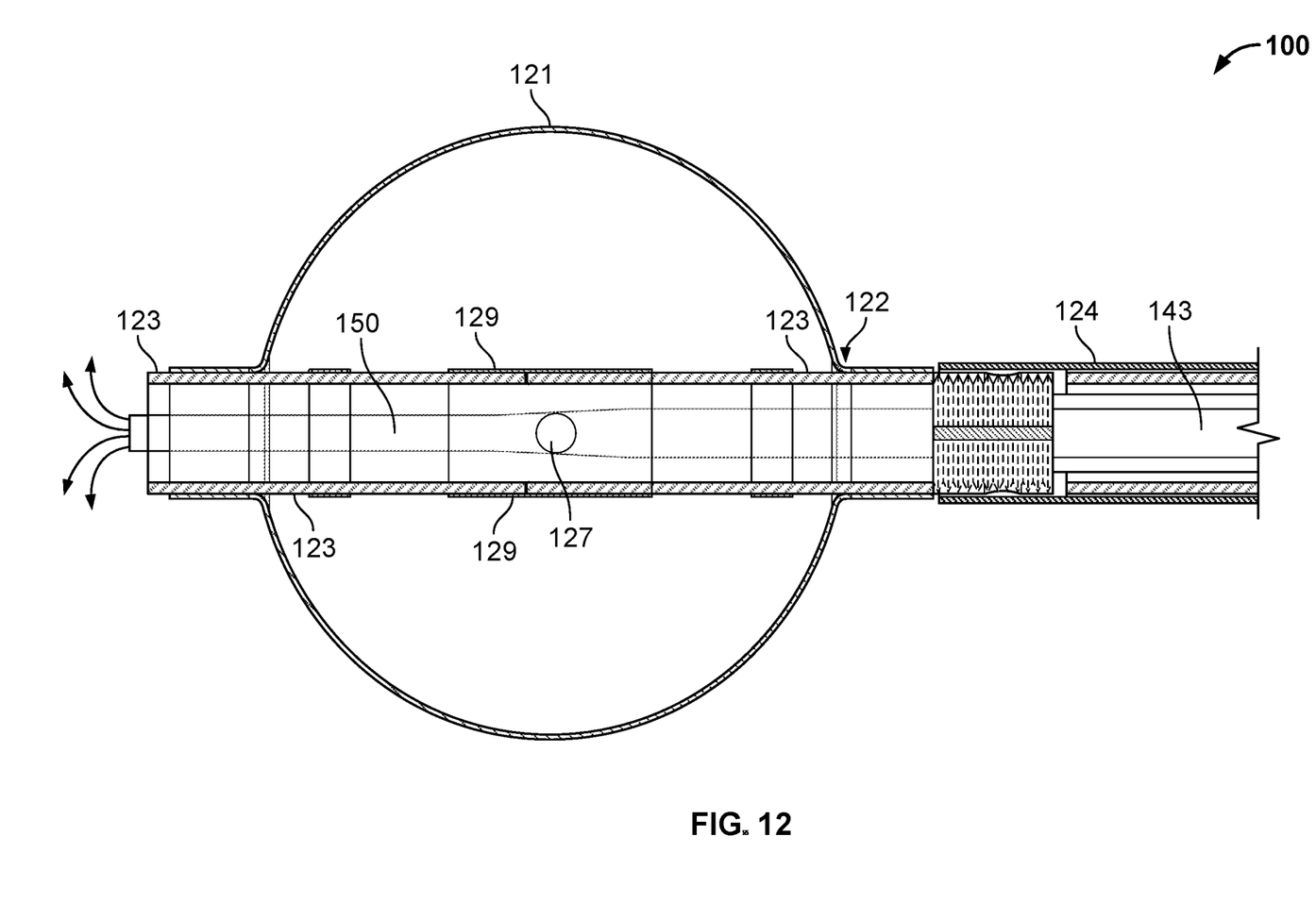
FIG. 12 illustrates a distal portion of an example kyphoplasty system being used to deliver vertebral body filler material.

For example, referring now to FIG. 12 for an illustrative example of the assembly that can be employed in step 265 (FIG. 4), the injection needle 150 can be slidably inserted through the balloon member delivery shaft 124 and into the central shaft 123 of the balloon implant member 122. The injection needle 150 defines a lumen 151 that injects filler material (e.g., orthopedic cement as described above) through the balloon member delivery shaft 124 and the balloon implant member 122. In some embodiments, the injection needle 150 is inserted through the balloon member delivery shaft 124 and the balloon implant member 122 and extends from a distal end of the balloon shaft 123.

In some embodiments, the injection needle 150 can include an external tab (e.g., similar to external tab 145 of the inflation plunger 140) that engages with and is received in the notch 131 when the injection needle 150 is slidably inserted through the balloon member delivery shaft 124 and into the central shaft 123 of the balloon implant member 122. The external tab of the injection needle 150 can engage with the notch 131 and can provide an anti-rotation mechanism when the tab is engaged with and is received in the notch 131. In some embodiments, another elongate instrument can be implemented in the kyphoplasty system 100 that includes a tab that is configured to provide an anti-rotation mechanism when the tab is engaged with and is received in the notch 131.

Referring again to FIG. 4, in step 270 of the process 200 filler material (e.g., orthopedic cement as described above) is injected into the vertebral body through the injection needle 150 that extends through the lumen of the kyphoplasty system 100. For example, as depicted in FIG. 12, in some embodiments the distal end of the balloon shaft 123 is open and the filler material can exit the lumen 151 of the injection needle 150 that extends through the lumen of the balloon implant member 122 and therefrom. Upon exiting the lumen 151 of the injection needle 150 and the lumen of balloon implant member 122, the filler material enters the vertebral body 12, exterior to the balloon 121 (e.g., as depicted in FIG. 3 in comparison to FIG. 2).

Figure 13A:
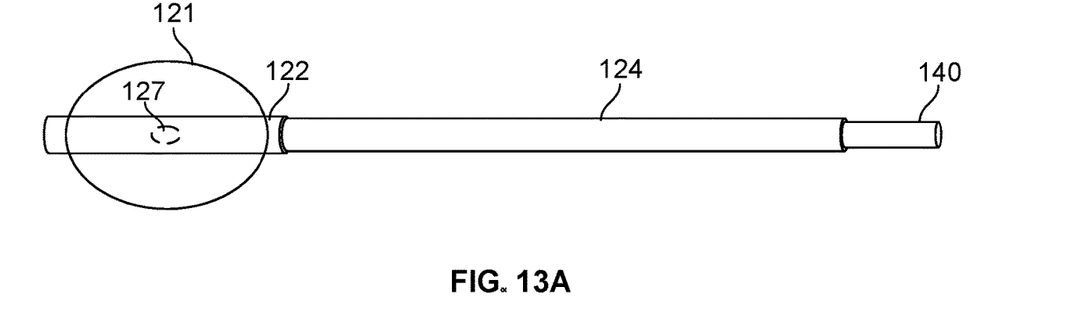
FIG. 13A illustrates an example kyphoplasty system with the balloon member in an expanded configuration.
Figure 13B:
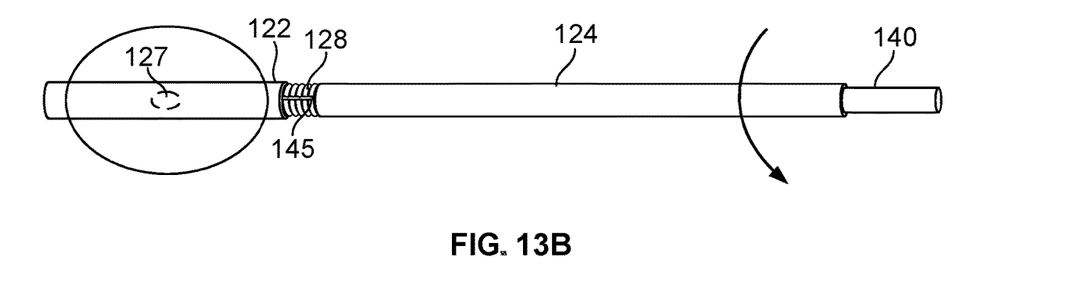
FIG. 13B illustrates the kyphoplasty system of FIG. 13A with the balloon implant device being detached from the delivery shaft.

Still referring to FIG. 4, in step 280 of the process 200, the inflation plunger is re-inserted to engage with an anti-rotation mechanism of the balloon implant device. For example, the inflation plunger 140 is advanced through the lumens of the implant member 122 and the balloon member delivery shaft 124, as depicted in FIGS. 11, 13A, and 13B, so that the tab 145 engages with and is received in the notch 131 and so that the inflation aperture 144 is aligned with the one or more apertures 127 of the balloon shaft 124. In some embodiments, the notch 131 and the tab 145 can provide an anti-rotation mechanism when the tab 145 is engaged with and is received in the notch 131.

Still referring to FIG. 4, in step 290 of the process 200, the delivery shaft is detached and removed from the balloon implant member while leaving the balloon implant member in the vertebral body. For example, when the practitioner P desires to detach the balloon member delivery shaft 124 from the balloon implant member 122 (as per step 280 of the balloon kyphoplasty procedure 200), the inflation plunger 140 is positioned so that the tab 145 engages with and is received in the notch 131. With the tab 145 engaged with the notch 131, the practitioner P holds a proximal end of the inflation plunger 140 (see e.g., FIG. 1) to prevent the inflation plunger 140 from rotating. The practitioner P can detach the balloon implant member 122 from the balloon member delivery shaft 124 by rotating the balloon member delivery shaft 124 with respect to the balloon implant member 122. Engagement between the tab 145 and the notch 131, along with the practitioner P securing the proximal end of the inflation plunger 140 facilitates rotation of the balloon member delivery shaft 124 with respect to the balloon implant member 122.

As depicted in FIG. 13B, rotation of the balloon member delivery shaft 124 with respect to the balloon implant member 122 unscrews the threaded connection between the threads 128 of the balloon implant member 122 and the threads 132 of the balloon member delivery shaft 124. That is, practitioner P can detach the balloon implant member 122 from the balloon member delivery shaft 124 by rotating the balloon member delivery shaft 124 while securing (e.g., via the inflation plunger 140) the balloon implant member 122 from rotation to remove the balloon member delivery shaft 124 from engagement with the balloon implant member 122. Then, the practitioner P can withdraw the balloon member delivery shaft 124 while leaving the balloon implant member 122 implanted in the vertebral body 12 (e.g., as depicted in FIG. 3).

Figure 13C:
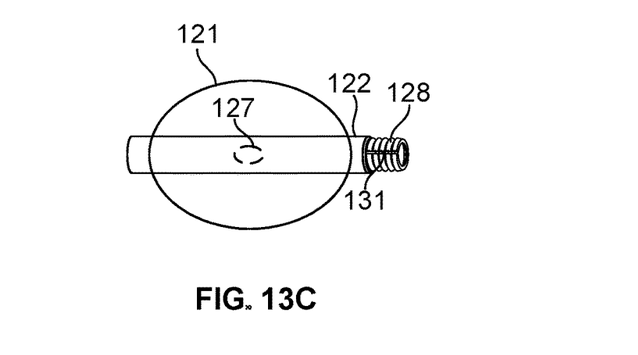
FIG. 13C illustrates the balloon implant device of FIG. 13A separated from the balloon implant delivery shaft.

Then, as illustrated in FIG. 13C, the practitioner P can withdraw the inflation plunger 140 while leaving the balloon implant member 122 implanted in the vertebral body 12 (e.g., as depicted in FIG. 3).

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination.

Moreover, although features may be described herein as acting in certain combinations and/or initially claimed as such, one or more features from a claimed combination can in some cases be excised from the combination, and the claimed combination may be directed to a subcombination or variation of a subcombination.

Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

What is claimed is:

1. A kyphoplasty system comprising:
    a balloon implant member comprising a balloon coaxially mounted on a balloon shaft so that the balloon shaft provides at least one balloon inflation port into an interior of the balloon, the balloon implant member including a notch that extends longitudinally through a portion of threads at a proximal end of the balloon implant member;
    a balloon member delivery shaft detachably connected to the balloon implant member via a threaded connection to the threads such that central lumens of the balloon member delivery shaft and the balloon shaft are axially aligned; and
    an inflation plunger defining an injection lumen and configured to slidingly advance through the central lumens of the balloon member delivery shaft and the balloon shaft to provide alignment of an exterior tab of the inflation plunger with the notch at the proximal end of the balloon implant member and to provide alignment of an inflation plunger aperture of the inflation plunger with the at least one balloon inflation port of the balloon implant member to inflate the balloon.

2. The kyphoplasty system of claim 1, wherein the inflation plunger aperture is positioned along a circumferential surface of a distal end portion of the inflation plunger so that an inflation medium delivered through the injection lumen is output into the interior of the balloon.

3. The kyphoplasty system of claim 2, wherein the balloon implant member further comprises at least one valve arranged proximate to the at least one balloon inflation port to allow flow of the inflation medium to inflate the balloon and to prevent the inflation medium from exiting the balloon.

4. The kyphoplasty system of claim 3, wherein the at least one valve includes at least one of a one-way flap valve or a one-way sleeve valve.

5. The kyphoplasty system of claim 1, wherein the exterior tab is positioned relative to the inflation plunger aperture along the inflation plunger so that, when the exterior tab mates with the notch, the inflation plunger aperture aligns with the balloon inflation port.

6. The kyphoplasty system of claim 1, wherein a distal end of the balloon member delivery shaft includes internal threads that are configured to releasably mate with the threads at the proximal end of the balloon implant member.

7. The kyphoplasty system of claim 1, wherein the exterior tab extends through the notch when the balloon implant member is releasably attached to a distal end portion of the balloon member delivery shaft.

8. The kyphoplasty system of claim 7, wherein the exterior tab engages with the notch to prevent rotation of the balloon implant member during rotation of the balloon member delivery shaft relative to the balloon implant member.

9. The kyphoplasty system of claim 7, wherein the exterior tab extends through the notch when the threads at the proximal end of the balloon implant member are releasably attached to internal threads at the distal end portion of the balloon member delivery shaft.

10. The kyphoplasty system of claim 1, wherein at least one of the balloon member delivery shaft, the balloon implant member, and the inflation plunger comprises markings configured to facilitate alignment of the balloon implant member, the balloon member delivery shaft, and the inflation plunger.

11. The kyphoplasty system of claim 10, wherein the markings are positioned on a proximal end of the inflation plunger.

12. The kyphoplasty system of claim 11, wherein the markings further include markings positioned on the balloon implant member that represent a rotational position of the balloon inflation port and the notch.

13. The kyphoplasty system of claim 1, further comprising:
    an injection needle defining an injection needle lumen and an injection needle tab, the injection needle configured to slidingly advance through the central lumen of the balloon member delivery shaft to provide alignment of the injection needle tab with the notch at the proximal end of the balloon implant member.

14. The kyphoplasty system of claim 13, wherein the injection needle extends from a distal end of the balloon member delivery shaft.

15. The kyphoplasty system of claim 1, wherein the inflation plunger has a tapered region such that an outer diameter of the inflation plunger is smaller at a distal end of the inflation plunger than at a proximal end of the inflation plunger.

16. The kyphoplasty system of claim 15, wherein the exterior tab is positioned distally of the tapered region.

17. The kyphoplasty system of claim 16, wherein the exterior tab extends outwardly from the inflation plunger to an exterior height so that an outermost lateral edge of the tab is no further from a central axis of the inflation plunger than the outer diameter of the inflation plunger at the proximal end.

18. The kyphoplasty system of claim 16, wherein the inflation aperture is positioned between the exterior tab and the distal end of the inflation plunger.

19. The kyphoplasty system of claim 16, wherein the exterior tab is positioned proximally from the inflation aperture.

20. The kyphoplasty system of claim 16, wherein the exterior tab and the inflation aperture are aligned with each other in a same central longitudinal plane of the inflation plunger.

\* \* \* \* \*